United States Patent
MacNeill et al.

(10) Patent No.: US 9,987,212 B2
(45) Date of Patent: Jun. 5, 2018

(54) ACETONE-DEFICIENT COMPOSITION

(71) Applicant: L'ORÉAL, Paris (FR)

(72) Inventors: Christopher Michael MacNeill, Fanwood, NJ (US); XianZhi Zhou, Millburn, NJ (US); Chunhua Li, Hillsborough, NJ (US); Hy Si Bui, Piscataway, NJ (US); Jean-Thierry Simonnet, Rueil Malmaison (FR)

(73) Assignee: L'ORÉAL, Paris (FR)

( * ) Notice: Subject to any disclaimer, the term of this patent is extended or adjusted under 35 U.S.C. 154(b) by 1 day.

(21) Appl. No.: 14/731,101

(22) Filed: Jun. 4, 2015

(65) Prior Publication Data
US 2016/0354295 A1 Dec. 8, 2016

(51) Int. Cl.
| | | |
|---|---|---|
| *C11D 3/20* | (2006.01) | |
| *C11D 3/43* | (2006.01) | |
| *C11D 3/44* | (2006.01) | |
| *A61K 8/49* | (2006.01) | |
| *A61K 8/34* | (2006.01) | |
| *A61K 8/362* | (2006.01) | |
| *A61Q 3/04* | (2006.01) | |
| *C11D 1/00* | (2006.01) | |
| *C11D 3/14* | (2006.01) | |
| *C11D 3/12* | (2006.01) | |
| *A61K 8/37* | (2006.01) | |
| *A61K 8/81* | (2006.01) | |

(52) U.S. Cl.
CPC .............. *A61K 8/4973* (2013.01); *A61K 8/34* (2013.01); *A61K 8/345* (2013.01); *A61K 8/362* (2013.01); *A61K 8/37* (2013.01); *A61K 8/8147* (2013.01); *A61Q 3/04* (2013.01); *C11D 1/00* (2013.01); *C11D 3/1206* (2013.01); *C11D 3/14* (2013.01); *C11D 3/201* (2013.01); *C11D 3/2003* (2013.01); *A61K 2800/30* (2013.01); *A61K 2800/43* (2013.01); *A61K 2800/48* (2013.01)

(58) Field of Classification Search
CPC ........... C11D 1/00; C11D 3/1206; C11D 3/14; C11D 3/2003; C11D 3/201; C11D 3/204; C11D 3/2044; C11D 3/222; C11D 3/225; C11D 3/2075; C11D 3/2093; C11D 3/401; B08B 3/04
USPC ....... 510/118, 123, 127, 201, 202, 203, 206, 510/211, 470, 505, 506; 134/42
See application file for complete search history.

(56) References Cited

U.S. PATENT DOCUMENTS

| | | | |
|---|---|---|---|
| 1,785,417 A * | 12/1930 | McEvoy ................. | C09D 9/00 510/206 |
| 2,528,378 A | 10/1950 | Mannheimer | |
| 2,781,354 A | 2/1957 | Mannheimer | |
| 4,735,798 A | 4/1988 | Bernstein | |
| 4,801,331 A * | 1/1989 | Murase ................. | A61K 8/042 106/173.01 |
| 4,927,556 A * | 5/1990 | Pokorny ................. | C09D 9/00 134/138 |
| 5,258,070 A | 11/1993 | Monteleone et al. | |
| 5,288,335 A * | 2/1994 | Stevens .................... | C09D 9/04 106/173.01 |
| 5,413,729 A * | 5/1995 | Gaul ...................... | C09D 9/005 252/364 |
| 5,691,290 A * | 11/1997 | Vonk ...................... | C09D 9/005 134/38 |
| 5,827,807 A | 10/1998 | Aoshima et al. | |
| 6,254,644 B1 * | 7/2001 | Traubel .............. | C08G 18/8083 428/473 |
| 6,358,901 B1 * | 3/2002 | Joye ....................... | C09D 9/005 134/38 |
| 6,369,009 B1 * | 4/2002 | MacHac, Jr. ............ | C09D 9/00 134/38 |
| 6,479,445 B1 * | 11/2002 | MacHac, Jr. ............ | C09D 9/00 134/38 |
| 6,482,270 B1 * | 11/2002 | MacHac, Jr. ........... | C09D 9/005 134/38 |
| 6,548,464 B1 * | 4/2003 | MacHac, Jr. ............ | C09D 9/00 134/38 |
| 6,566,316 B2 * | 5/2003 | Hiatt ........................ | C09D 9/00 134/3 |
| 6,586,380 B2 * | 7/2003 | Marquis .................. | C09D 9/00 134/38 |
| 6,673,157 B1 * | 1/2004 | McKim .................. | C09D 9/005 134/2 |
| 8,835,369 B2 | 9/2014 | Cifelli | |
| 2002/0111284 A1 * | 8/2002 | MacHac, Jr. ............ | C09D 9/00 510/245 |
| 2003/0032570 A1 * | 2/2003 | Hiatt ........................ | C09D 9/00 510/201 |
| 2003/0119686 A1 * | 6/2003 | MacHac, Jr. ............ | C09D 9/00 510/201 |
| 2004/0235690 A1 * | 11/2004 | Oldenhove .......... | C11D 3/0089 510/130 |
| 2005/0202982 A1 * | 9/2005 | Perlman ................ | A61K 8/4973 510/118 |

(Continued)

FOREIGN PATENT DOCUMENTS

JP       2014-139142 A       7/2014

OTHER PUBLICATIONS

International Search Report and Written Opinion dated Aug. 8, 2016 in PCT/US2016/034069.

*Primary Examiner* — Gregory R Delcotto
(74) *Attorney, Agent, or Firm* — Oblon, McClelland, Maier & Neustadt, L.L.P.

(57) ABSTRACT

An acetone deficient composition including at least one polyol, at least one alkyl carbonate, at least one monoalcohol and optionally at least one hydrocarbon based non-volatile oil is provided.

4 Claims, No Drawings

(56) References Cited

U.S. PATENT DOCUMENTS

| | | | |
|---|---|---|---|
| 2006/0089281 A1* | 4/2006 | Gibson | C09D 9/005 510/201 |
| 2008/0161217 A1* | 7/2008 | Zhang | G03F 7/426 510/176 |
| 2012/0046212 A1* | 2/2012 | Bourdette | C09D 9/04 510/206 |
| 2012/0231987 A1* | 9/2012 | Britton | C11D 1/83 510/138 |
| 2013/0148911 A1* | 6/2013 | Peterson | G06T 3/4038 382/284 |
| 2013/0319462 A1 | 12/2013 | Cifelli | |
| 2014/0315773 A1 | 10/2014 | Holman et al. | |
| 2015/0038391 A1* | 2/2015 | De Wit | C11D 11/0023 510/238 |

* cited by examiner

ACETONE-DEFICIENT COMPOSITION

FIELD OF THE INVENTION

The present invention relates to a composition comprising at least one polyol, at least one alkyl carbonate, optionally at least one hydrocarbon based non-volatile oil, at least one monoalcohol, optionally at least one colorant, optionally at least one abrasive agent, optionally at least one thickening polymer, optionally at least one surfactant and optionally water, wherein the composition is essentially free of acetone and free of odor associated with acetone derivatives. The combination of polyol, alkyl carbonate and optional hydrocarbon based non-volatile oil is also referred to as an "odorless base". Preferably, the inventive composition is an acetone free nail polish remover or cleanser. Owing to the unique properties of the inventive nail polish remover, the composition is particularly effective in removal of water based nail compositions (enamels).

DISCUSSION OF THE BACKGROUND

Traditional nail polish removers can contain a large amount of organic solvents such as acetone, ethyl acetate and/or butyl acetate, primarily because they provide good removability properties. However, these compounds have a very strong, long-lasting odor which is not desirable by consumers. In addition, they are harsh on nails and cuticles.

Nail polish removers which do not utilize acetone or other organic solvent are also known. Such compositions have been described for example in U.S. Pat. No. 8,835,369 the entire content of which is hereby incorporated by reference. While the composition of '369 is organic solvents free, it is not effective to remove water based nail enamels.

Nail polish removers suitable for removal of water based nail compositions have been attempted. For example, U.S. Pat. No. 5,827,807 describes a nail polish remover utilizing acetone, ethylene carbonate and alcohol. Another proposed solution for a remover of water based nail enamels is disclosed in U.S. Pat. No. 4,735,798. The compositions according to '798 contain acetone, ethyl acetate, ethyl alcohol, glycerin and water. Although, the nail polish removers offered by '807 and 798 are useful in removal of water based nail compositions, the down side is that they contain acetone may not be desirable from consumer point of view.

There remains a need to develop nail polish remover compositions that are acetone deficient and have high efficacy in removing water based nail enamels.

Without being bound by theory, it is believed that monoalcohol, alkylene carbonate and polyol have synergistic effect on removal of water based enamels containing acrylic polymer(s). It was observed that the monoalcohol partially dissolves and swells the acrylic film of the water based nail enamel. Simultaneously, polyol enhances the removal process by softening the acrylic film. Further, alkylene carbonate acts as both a solvent to partially dissolve the acrylate film and a plasticizer to soften the film. It was discovered that a specific ratio of the "odorless base" to monoalcohol is important in developing an effective polish remover for water based nail enamels containing the acrylic film former(s).

SUMMARY OF THE INVENTION

The present invention relates to an acetone deficient composition comprising:

(a) at least one odorless base comprising:
   at least one polyol;
   at least one alkylene carbonate;
   optionally at least one hydrocarbon based non-volatile oil; and
(b) at least one alcohol;

A further aspect of the present invention relates to an acetone deficient nail polish remover as described above optionally further comprising at least one thickening polymer, optionally at least one abrasive agent, optionally at least one surfactant, optionally at least one pigment and optionally water, and mixtures thereof.

Another embodiment of the present invention relates to a method of removing a water based nail polish, comprising treating nails with acetone deficient nail polish remover described above.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Abrasive" or "surface disrupting agent" means a rough material causing disruption of a surface and increase the roughness of the surface to improve removal of the coating from a surface.

"At least one", as used herein, means one or more, and thus the term includes individual components as well as mixtures or combinations.

"Acetone Deficient" or "essentially free of acetone" or "devoid of acetone" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "acetone deficient" means that acetone or acetone derivative(s) is preferably omitted from a composition (that is 0% by weight or "free of acetone"), but can be present in the composition at an amount of less than about 0.25% by weight, typically less than about 0.1% by weight, typically less than about 0.05% by weight, based on the total weight of the composition as a whole.

"Emulsifier" or "emulsifying surfactant" or "surfactant" is a term of art that is well known to those skilled in the art. See, e.g. http://pharmlabs.unc.edu/labs/emulsions/agents.htm. It is a compound that has a hydrophilic part and a lipophilic part ("amphiphilic") and facilitates the dispersion of two mutually insoluble phases, in this case the dispersion of a liquid fatty substance in water.

"Essentially free of odor" or "odorless" or "odor free", used interchangeably herein, mean that there is no or essentially no detectable level of odor due to acetone, ethyl acetate or other acetone derivatives that an ordinary consumer can perceive.

"High removability" or "high removability efficiency" or "high removal efficiency", used interchangeably herein, means an effective removal to an ordinary consumer of a coating from a nail by a nail remover composition.

"Hydrocarbon-based oil" means oil formed essentially from hydrogen and carbon and free of heteroatoms such as N, Si, F and P. The hydrocarbon-based oil is thus different from a silicone oil or a fluoro oil.

"Nails", "fingernail or "toenail" refers to a human keratinous substrate which can be treated (decorated) with a single or multiple nail cosmetic compositions.

"Nail polish remover", as used herein, means a substance substantially removing a coating of nail polish (enamel) from the nail and/or area surrounding the nail using a composition or an artificial nails such as nail spoons.

"Non-volatile oil" means an oil whose vapour pressure at room temperature and atmospheric pressure is non-zero and is less than 0.02 mmHg (2.66 Pa) and better still less than $10^{-3}$ mmHg (0.13 Pa).

"Substantially" or "substantially removed" or "noticeably removed" or "almost completely removed", used interchangeably herein, mean that the majority (central part) of nail polish compositions covering the surface of the nail (human or artificial) is removed with nail polish removers.

"Thickening polymer" or "thickening polymers" or "thickeners" mean substances increasing viscosity of liquids.

"Water based nail polish" or "water based nail enamel" means that the composition contains water at minimum of 10% or more.

The compositions and methods of the present invention can comprise, consist of, or consist essentially of the essential elements and limitations of the invention described herein, as well as any additional or optional ingredients, components, or limitations described herein or otherwise useful.

In an embodiment, the invention relates to an acetone deficient composition comprising:
(a) at least one odorless base comprising:
  at least one polyol;
  at least one alkylene carbonate; and
  optionally at least one hydrocarbon based non-volatile oil;
(b) at least one monoalcohol;
(c) optionally at least one thickening polymer;
(d) optionally at least one abrasive agent;
(e) optionally at least one surfactant;
(f) optionally at least one pigment; and
(g) optionally water;
  wherein the ratio of at least one odorless base (a) to at least one monoalcohol (b) is from about 90:10 to about 10:90, by weight, relative to the total weight of the composition.

In another embodiment, the invention relates to an acetone deficient composition comprising:
(a) at least one odorless base comprising:
  at least one polyol;
  at least one alkylene carbonate; and
  optionally at least one hydrocarbon based non-volatile oil;
(b) at least one monoalcohol;
(c) optionally at least one thickening polymer;
(d) optionally at least one abrasive agent;
(e) optionally at least one surfactant;
(f) optionally at least one pigment; and
(g) optionally water;
  wherein the ratio of at least one alkylene carbonate to at least one monoalcohol is from about 6:1 to about 1:12 and the ratio of at least one polyol to at least one monoalcohol is from about 1:1 to about 1:20, by weight, relative to the total weight of the composition.

In another embodiment, the invention relates to an acetone deficient composition comprising:
(a) at least one odorless base comprising:
  at least one polyol;
  at least one alkylene carbonate;
  at least one hydrocarbon based non-volatile oil; and
(b) at least one monoalcohol;
(c) optionally at least one thickening polymer;
(d) optionally at least one abrasive agent;
(e) optionally at least one surfactant;
(f) optionally at least one pigment; and
(g) optionally water;
  wherein the ratio of at least one monoalcohol to at least one hydrocarbon based non-volatile oil is from about 28:1 to about 1.5:1, by weight, relative to the total weight of the composition.

In another embodiment, the invention relates to an acetone deficient composition comprising:
(a) from about 10% to about 90% by weight of at least one odorless base comprising:
  from about 2% to about 15% by weight of at least one polyol; from about 10% to about 95% by weight of at least one alkylene carbonate;
  optionally from about 1.5% to about 13.5% by weight of at least one hydrocarbon based non-volatile oil; and
(b) from about 10% to about 95% by weight of at least one monoalcohol;
(c) optionally from about 0.5% to about 5% by weight of at least one thickening polymer;
(d) optionally from about 0.5% to about 5% by weight of at least one abrasive agent;
(e) optionally from about 0.1% to about 2% by weight of at least one surfactant;
(f) optionally from about 0.1% to about 5% by weight of at least one pigment; and
(g) optionally from about 0.5% to about 20% by weight of water.

In the immediately preceding embodiments, the viscosity for liquid inventive compositions is preferably from about 0.0001 Pa·s to about 10 Pa·s as measured at room temperature (25° C.) by Brookfield Synchro-Electric viscometer using spindle RV-4 at a shear rate of 1 RPM.

In the another embodiments, the viscosity for gel inventive compositions is preferably from about 10 Pa·s to about 250 Pa·s as measured at room temperature (25° C.) by Brookfield Synchro-Electric viscometer using spindle RV-4 at a shear rate of 1 RPM.

The above compositions are preferably used as nail polish removers. Thus, the present invention preferably relates to a method of removing water based nail enamels using the acetone deficient compositions as disclosed in the immediately preceding embodiments.

The present invention also relates to a kit for a nail enamel remover comprising (1) an acetone deficient composition as defined above, (2) at least one container for the acetone deficient composition as defined above and (3) optionally an applicator for the acetone deficient composition as defined above.

Preferably, the kit for a nail composition system further comprises instructions for removing a water based nail enamel composition system by employing an acetone deficient nail polish remover as defined above.

"Odorless Base"

The inventive compositions comprise an "odorless base" containing at least one polyol, at least one alkylene carbonate and optionally at least one hydrocarbon-based non-volatile oil.

The amount of the "odorless base" ranges from about 5% to about 90%, preferably from about 20% to about 80%, more preferably from about 30% to about 70%, most typically from about 40% to about 60%, including all ranges and subranges therebetween, by weight relative to the total weight of the acetone deficient compositions.

As per the instant invention the acetone deficient compositions contain the at least one "odorless base" and at least one monoalcohol. According to preferred embodiments, the ratio of the at least one "odorless base" to the at least one monoalcohol ranges from about 10% to about 95%, preferably from about 20% to about 80%, more preferably from about 30% to about 70%, most typically from about 40% to about 60%, including all ranges and subranges therebetween, by weight, relative to the total weight of the compositions.

In terms of weight ratio, the weight ratio of at least one odorless base (a) to at least one monoalcohol (b) is preferably from about 90:10 to about 10:90, preferably from about 67:33 to about 33:67, and preferably from about 60:40 to about 40:60, including all ranges and subranges therebetween.

Polyol(Polyol Solvent)

The inventive compositions of acetone deficient nail polish remover also comprise at least one polyol in an amount preferably ranging from about 2% to about 15%, preferably from about 8% to about 12%, most typically from about 5% about 9%, including all ranges and subranges therebetween, by weight relative to the total weight of the compositions.

These at least one polyol may be selected from glycols and glycol ethers, specifically at least one polyols may be selected from $C_3$-$C_5$ glycols, in particular selected from the group consisting of 1,2-propylene glycol, 1,2-butylene glycol, dipropylene glycol or diethylene glycol and 1,2-pentylene glycol. Preferably, the at least one $C_3$-$C_5$ glycol is 1,2-propylene glycol, which is commonly known as propylene glycol.

Alkylene Carbonate

The inventive compositions of acetone deficient nail polish remover comprise at least one alkylene carbonate in an amount preferably ranging from about 10% to about 95%, preferably from about 20% to about 85%, most typically from about 30% about 65%, including all ranges and subranges therebetween, by weight relative to the total weight of the compositions.

The at least one alkylene carbonate may be selected from $C_4$-$C_6$ cyclic carbonates, particularly selected from the group consisting of propylene carbonate, dipropylene carbonate, butylene carbonate, 2,3-butylene carbonate, 2,3-pentylene carbonate, pentylene carbonate, ethylene carbonate. Preferably, the at least one $C_4$-$C_6$ cyclic carbonate is propylene carbonate.

Hydrocarbon-Based Non-Volatile Oil (Optional)

The inventive compositions of acetone deficient nail polish removers may comprise the at least one hydrocarbon-based non-volatile oil in an amount preferably ranging from about 1.5% to about 13.5%, preferably from about 3% to about 12%, most typically from about 6% to about 9%, including all ranges and subranges therebetween, by weight, relative to the total weight of the compositions.

The composition according to the invention comprises at least one hydrocarbon-based non-volatile oil, chosen from: $C_{10}$-$C_{26}$ monoalcohols; hydroxylated monoesters of a $C_2$-$C_8$ carboxylic acid and of a $C_2$-$C_8$ alcohol; hydroxylated diesters of a $C_2$-$C_8$ dicarboxylic acid and of a $C_2$-$C_8$ alcohol; hydroxylated triesters of a $C_2$-$C_8$ tricarboxylic acid and of a $C_2$-$C_8$ alcohol and esters of a $C_2$-$C_8$ polyol and of one or more $C_2$-$C_8$ carboxylic acids.

In the present case, the said non-volatile hydrocarbon-based oil comprises at least one oxygen atom. In particular, the said non-volatile hydrocarbon-based oil comprises at least one alcohol function (it is then "alcohol oil") and/or at least one ester function (it is then "ester oil").

The ester oils that may be used in the compositions according to the invention may especially be hydroxylated.

According to a particularly preferred embodiment, the said first oil is a $C_{10}$-$C_{26}$ alcohol, preferably a monoalcohol, which is preferably branched when it comprises at least 16 carbon atoms.

Preferably, the $C_{10}$-$C_{26}$ alcohols are saturated or unsaturated, and branched or unbranched, and comprise from 10 to 26 carbon atoms. Preferably, the $C_{10}$-$C_{26}$ alcohols are fatty alcohols, which are preferably branched when they comprise at least 16 carbon atoms.

As examples of fatty alcohols that may be used according to the invention, mention may be made of linear or branched fatty alcohols, of synthetic origin or alternatively of natural origin, for instance alcohols derived from plant material (coconut, palm kernel, palm, etc.) or animal material (tallow, etc.). Needless to say, other long-chain alcohols may also be used, for instance ether alcohols or Guerbet alcohols. Finally, use may also be made of certain more or less long fractions of alcohols of natural origin, for instance coconut ($C_{12}$ to $C_{16}$) or tallow ($C_{16}$ to $C_{18}$) or compounds of diol or cholesterol type.

Use is preferably made of a fatty alcohol comprising from 10 to 24 carbon atoms and more preferentially from 12 to 22 carbon atoms.

As particular examples of preferred fatty alcohols that may be used in the context of the present invention, mention may be made especially of lauryl alcohol, myristyl alcohol, isostearyl alcohol, palmityl alcohol, oleyl alcohol, behenyl alcohol, erucyl alcohol, arachidyl alcohol, 2-hexyldecyl alcohol, isocetyl alcohol and octyldodecanol, and mixtures thereof.

The non-volatile hydrocarbon-based oil may be chosen from octyldodecanol and isostearyl alcohol, and mixtures thereof.

According to a embodiment, the said non-volatile hydrocarbon-based oil is an ester oil chosen from: hydroxylated monoesters of a $C_2$-$C_8$ carboxylic acid and of a $C_2$-$C_8$ alcohol; hydroxylated diesters of a $C_2$-$C_8$ dicarboxylic acid and of a $C_2$-$C_8$ alcohol; such as diisopropyl adipate, 2-diethylhexyl adipate, dibutyl adipate or diisostearyl adipate, hydroxylated triesters of a $C_2$-$C_8$ tricarboxylic acid and of a $C_2$-$C_8$ alcohol, such as citric acid esters, such as trioctyl citrate, triethyl citrate, acetyl tributyl citrate, tributyl citrate or acetyl tributyl citrate, esters of a $C_2$-$C_8$ polyol and of one or more $C_2$-$C_8$ carboxylic acids, such as glycol diesters of monoacids, such as neopentyl glycol diheptanoate, preferably glycol triesters of monoacids.

As per this invention, the preferred glycol triesters of monoacids are selected from triesters of glycerol and $C_2$-$C_5$ carboxylic acids.

Glycerol is also commonly referred to as glycerin or glycerine and has the IUPEC name of propane-1,2,3-triol. The $C_2$-$C_5$ carboxylic acid can be selected from acetic acid, propionic acid, butyric acid and valeric acid. Therefore, the at least one triester of glycerol and $C_2$-$C_5$ carboxylic acid can be selected from the group consisting of glycerol triacetate (also referred to as triacetin), glycerol tripropionate, glycerol tributyrate and glycerol trivalerate. Preferably, the at least one triester of glycerol and $C_2$-$C_5$ carboxylic acid is triacetin known for example as EDENOR GTA (EMERY OLEOCHEMICALS) and Polarin T Deo (Cognis).

Monoalcohol(s)

The inventive compositions also comprise at least one monoalcohol, preferably at least one a short chain monoalcohol in an amount ranging from about 10% to about 95%, preferably from about 20% to about 85%, most typically from about 30% about 65%, including all ranges and subranges therebetween, by weight relative to the total weight of the compositions.

The compositions of the invention include at least one monoalcohol comprising 2 to 8 carbon atoms, in particular 2 to 6 carbon atoms and more particularly 2 to 4 carbon atoms. The compositions of the invention may include one or more monoalcohol.

This monoalcohol may be represented, for example, by the formula $R_aOH$, in which $R_a$ represents a linear or branched alkyl group containing:

a=2 to 8 carbon atoms

As examples of monoalcohols, ethanol, isopropanol, propanol and butanol may be cited.

According to an embodiment, the compositions of the invention include ethanol.

According to preferred embodiments, the weight ratio of at least one alkylene carbonate to at least one monoalcohol is preferably from about 12:1 to about 1:24, preferably from about 6:1 to about 1:12, and the weight ratio of at least one polyol to at least one monoalcohol is preferably from about 3:1 to about 1:30, preferably from about 1:1 to about 1:20, all of these ranges including all subranges therebetween.

Water (Optional)

The inventive compositions may also comprise water in an amount preferably ranging from about 0.5% to about 20%, preferably from about 0.5% to about 18%, typically from about 1% to about 10%, most typically from about 1% about 5% including all ranges and subranges therebetween, by weight, relative to the total weight of the compositions.

Surfactants (Optional)

The composition in accordance with the invention comprises optionally at least one surfactant present in an amount preferably ranging from about 0.1% to about 2% by weight, preferably from about 0.2% to about 1.5% and more particularly from 0.5% to 1% by weight, relative to the weight of the composition.

As per this invention, at least one surfactant with at least one fatty chain containing at least 8 and preferably between 8 and 22 carbon atoms. The surfactant may be anionic, amphoteric or zwitterionic, nonionic and cationic.

As examples of anionic surfactant that may be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, a-olefin sulfonates, paraffin sulfonates; alkyl sulfosuccinates, alkyl ether sulfosuccinates, alkylamide sulfosuccinates; alkyl sulfoacetates; acyl sarcosinates and acyl glutamates. It is also possible to use alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates. As per this invention, alkyl sulfates may be particularly useful, specifically sodium lauryl sulfate (SLS). Enter trade anmes+vendors.

The alkyl or acyl radical of all of these different compounds preferably contains from 12 to 20 carbon atoms and the aryl radical preferably denotes a phenyl or benzyl group.

Among the anionic surfactant that may also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated alkyl ether carboxylic acids, polyoxyalkylenated alkylaryl ether carboxylic acids, polyoxyalkylenated alkylamido ether carboxylic acids and their salts, in particular those containing from 2 to 50 alkylene oxide groups in particular ethylene oxide groups, and mixtures thereof.

The nonionic surfactants are, themselves also, compounds that are well known per se (see in particular in this respect "Handbook of Surfactants" by M. R. Porter, published by Blackie and Son (Glasgow and London), 1991, pp. 116-178). Thus, they can be chosen in particular from polyethoxylated, polypropoxylated, alkylphenols, alpha-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides or N-acylaminopropylmorpholine oxides.

The amphoteric or zwitterionic surfactants, can be, in particular, aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido($C_1$-$C_6$) alkylbetaines or ($C_8$-$C_{20}$)alkylamido($C_1$-$C_6$)alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Capryloamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Among the cationic surfactants, mention may be made in particular of: salts of optionally polyoxyalkylenated primary, secondary or tertiary fatty amines; quaternary ammonium salts such as tetraalkylammonium, alkylamido-alkyltrialkylammonium, trialkylbenzylammonium, trialkylhydroxyalkylammonium or alkylpyridinium chlorides or bromides; imidazoline derivatives; or amine oxides of cationic nature.

Thickening Polymer (Optional)

The inventive compositions may also comprise at least one thickening polymer in an amount preferably ranging from about 0.5% to about 5%, preferably from about 1% to about 3%, most typically from about 1.5% about 2.5%, including all ranges and subranges therebetween, by weight, relative to the total weight of the compositions.

Among the thickening polymers applicable in this invention are synthetic thickening polymer and natural thickening polymers. The synthetic polymers in accordance in accordance with various exemplary embodiments may be anionic, cationic, nonionic or amphoteric.

By the way of examples, the synthetic polymers include acrylic based polymers, non-crosslinked polymers, preferably crosslinked polymers.

Additionally, crosslinked thickening polymers may be chosen according to further exemplary embodiments. For example, such polymers may be chosen from polymers resulting from the polymerization of a mixture of monomers comprising:
  acrylic acid,
  an ester of formula (III) described above, in which $R_2$ is chosen from H or $CH_3$, $R_3$ denoting an alkyl radical having from 12 to 22 carbon atoms, and
  a crosslinking agent, which is a well-known copolymerizable polyethylenic unsaturated monomer, such as diallyl phthalate, allyl (meth)acrylate, divinylbenzene, (poly)ethylene glycol dimethacrylate and methylenebisacrylamide.

By way of example, crosslinked thickening polymers comprising about 60% to about 95% by weight of acrylic acid (hydrophilic unit), about 4% to about 40% by weight of $C_{10}$-$C_{30}$ alkyl acrylate (hydrophobic unit), and about 0% to about 6% by weight of crosslinking polymerizable monomer.

In yet further embodiments, the crosslinked thickening polymers may comprise about 96% to about 98% by weight of acrylic acid (hydrophilic unit), about 1% to about 4% by weight of $C_{10}$-$C_{30}$ alkyl acrylate (hydrophobic unit), and about 0.1% to 0.6% by weight of crosslinking polymerizable monomer, such as those described above. Examples of such polymers include acrylate/$C_{10}$-$C_{30}$ alkyl acrylate copolymers (INCI name: Acrylates/C10-30 Alkyl Acrylate Crosspolymer), such as the products sold by Lubrizol under the trade names PEMULENT™ TR1, PEMULEN™ TR2, CARBOPOL® 1382 and CARBOPOL® EDT 2020 may be chosen.

Abrasive Agents/Fillers (Optional)

The acetone deficient nail polish composition according to the invention may further comprise one or a plurality of abrasive agents.

In this particular invention, abrasive agents can be present particularly at a content preferably ranging from about 0.5% to about 5% by weight, preferably ranging from about 1% to about 3% by weight, most preferably from about 1.5% to about 2%, including all ranges and subranges therebetween, by weight, relative to the total weight of the compositions.

The term "abrasive agents" should be understood to refer to inorganic or synthetic colorless or white particles of any shape, insoluble in the medium of the composition regardless of the temperature at which the composition is manufactured. The abrasive agents may particularly be used to modify the rheology or texture of the composition.

In this particular invention, it has been found that abrasive agents increase adhesion between the basecoat and the second coat (color coat) of the nail system. It is believed that the increased adhesion between the basecoat and the second coat (color coat) due to the presence of said abrasive agents allows for easier peel removal of the nail treatment application (peel off in one piece) without leaving any remaining film on the nail plate.

The abrasive agents may be mineral or organic particles of any shape, in sheet, spherical or oblong form, regardless of the crystallographic shape (for example sheet, cubic, hexagonal, orthorhombic, etc). Mention may be made of talc, mica, silica, kaolin, polyamide (Nylon®) (Orgasol® from Atochem), poly-β-alanine and polyethylene powders, tetrafluoroethylene polymer powders (Teflon®), lauroyl-lysine, starch, boron nitride, polymeric hollow microspheres such as those of polyvinylidene chloride/acrylonitrile like Expancel® (Nobel Industrie), acrylic acid copolymers (Polytrap® from Dow Corning) and silicone resin microbeads (Tospearls® from Toshiba, for example), elastomer polyorganosiloxane particles, precipitated calcium carbonate, magnesium carbonate and hydro-carbonate, hydroxyapatite, hollow silica microspheres (Silica Beads® from Maprecos), glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate. One of the preferred abrasive agents used in this invention are precipitated silicas having wax treated surface, such as Silica (and) Polyethylene (ACEMATT OK 412® from Evonic). Another useful abrasive agents belong to the group of synthetically silicated clays, such as Lithium Magnesium Sodium Silicate (LAPONITE XLG® from BYK Additives Instruments).

Coloring Agent (Optional)

According to one embodiment, the acetone deficient nail polish remover may further comprise at least one coloring agent chosen from the group consisting of soluble dyes, pigments, nacres and glitter.

The composition according to the invention according to this embodiment is typically used as colored nail varnish.

The term "soluble dyes" should be understood to refer to organic, inorganic or organometallic compounds, soluble in the composition according to the invention and intended to color said composition.

The dyes are, for example, Sudan Red, DC Red 17, DC Green 6, β-carotene, soybean oil, Sudan brown, DC Yellow 11, DC Violet 2, DC Orange 5 and Quinoline Yellow.

The term "pigments" should be understood to refer to inorganic or organic, white or colored particles of any shape, insoluble in the composition according to the invention and intended to color said composition.

The term "nacres" should be understood to refer to iridescent particles of any shape, particularly produced by some mollusks in their shell or by synthetic means.

The pigments may be white or colored, inorganic and/or organic. Of the inorganic pigments, mention may be made of titanium dioxide, optionally surface-treated, zirconium or cerium oxides, along with zinc, iron (black, yellow or red) or chromium oxides, manganese violet, ultramarine blue, chromium hydrate and iron blue, metallic powders such as aluminum powder, copper powder.

Of the organic pigments, mention may be made of carbon black, D & C type pigments, and lacquers based on cochineal carmine, barium, strontium, calcium, aluminum.

Mention may also be made of effect pigments such as particles comprising a natural or synthetic organic or inorganic substrate, for example glass, acrylic resins, polyester, polyurethane, polyethylene terephthalate, ceramics, aluminas and optionally coated with metallic substances such as aluminum, gold, copper, bronze, or with metal oxides such as titanium dioxide, iron oxide, chromium oxide, inorganic or organic pigments and mixtures thereof.

The pearlescent pigments may be chosen from white pearlescent pigments such as mica coated with titanium, or bismuth oxychloride, colored pearlescent pigments such as titanium mica coated with iron oxides, titanium mica coated with iron blue and chromium oxide in particular, titanium mica coated with an organic pigments of the aforementioned type and pearlescent pigments based on bismuth oxychloride.

Pigments with goniochromatic properties may be used, particularly liquid crystal or multilayer pigments.

Optical brighteners or fibers optionally coated with optical brighteners may also be used.

The at least one coloring agent is preferably present in a total content greater than or equal to 0.1% by weight in relation to the inventive composition, ranging preferably from about 0.1 to about 5%, advantageously from about 0.2 to about 2%, including all ranges and subranges therebetween, by weight, relative to the total weight of the compositions.

Auxiliaries/Additives (Optional)

The acetone deficient nail polish remover of the present invention may additionally comprise an additive or auxiliary commonly used in cosmetic compositions and known to a person skilled in the art as being capable of being incorporated into said compositions. Such additives or auxiliaries may be chosen from thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

The at least one additive is present in a total content greater than or equal to 0.001% by weight in relation to the total weight of the inventive composition, ranging preferably from about 0.01 to about 2.5%, advantageously from about 0.1 to about 1%, including all ranges and subranges therebetween, by weight, relative to the total weight of the compositions.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

EXAMPLES

The following Examples are intended to be non-restrictive and explanatory only, with the scope of the invention being defined by the claims.

Method of Preparation of Inventive Compositions

The liquid inventive compositions were prepared according to the following procedure:

1. The odorless base was prepared by mixing together propylene glycol, propylene carbonate and triacetin for 2 minutes at 25° C. using a high speed mixer by Flaktek Inc. DAC 400.1 FVZ at 2500 RPM.
2. In order to determine the best working alcohol, the odorless base was combined with ethanol, isopropanol and butanol respectively at ratios specified below. The blends were mixed for 2 minutes using the same mixer as indicated above under the same conditions. The tested ratios of alcohols and the odorless base were as follows: 20% of alcohol:80% of the odorless base, 400 of alcohol:60% of the odorless base, 60% of alcohol: 40% of the odorless base and 80% of alcohol: 20% of the odorless base.

The gel inventive composition was prepared by the following method:

1. Carbopol was combined with water and pre-mixed for 2 minutes at 25° C. using a high speed mixer by Flaktek Inc. DAC 400.1 FVZ at 2500 RPM.
2. Subsequently, ethanol was added and the composition was mixed again for 2 minutes using the same mixer under conditions as disclosed above.
3. The remaining compounds (propylene glycol, propylene carbonate and triacetin) were added and mixed for 2 minutes using the same mixer under the same conditions.

TABLE 1

Inventive and Comparative Compositions
Inventive compositions of the acetone deficient nail polish remover are represented but not limited by examples in Table 1, shown below.

| Ingredients | inventive 1 gel (% wt)* | inventive 2 (% wt)* | inventive 3 (% wt)* | inventive 4 (% wt)* | comparator 1 (% wt)* | comparator 2 (% wt)* |
|---|---|---|---|---|---|---|
| ALCOHOL DENAT. (Ethanol) | 48 | 60 | 48 | 48.0 | | |
| WATER | 18 | — | 19 | 15.50 | 0.059940 | |
| TRIACETIN | 4.80 | 6.00 | 4.80 | 4.80 | 14.94 | 15 |
| PROPYLENE CARBONATE | 20.80 | 26 | 20.80 | 20.80 | 65 | 65 |
| PROPYLENE GLYCOL | 6.40 | 8 | 6.40 | 6040 | 20 | 20 |
| ACRYLATES/ C10-30 | 2.0 | — | 1.0 | 2.0 | — | |

TABLE 1-continued

Inventive and Comparative Compositions
Inventive compositions of the acetone deficient nail polish remover are represented but not limited by examples in Table 1, shown below.

| Ingredients | inventive 1 gel (% wt)* | inventive 2 (% wt)* | inventive 3 (% wt)* | inventive 4 (% wt)* | comparator 1 (% wt)* | comparator 2 (% wt)* |
|---|---|---|---|---|---|---|
| ALKYL ACRYLATE CROSSPOLYMER | | | | | | |
| TRIDECETH-6 | 2.0 | — | 1.0 | 2.0 | — | — |
| PEG-30 DIPOLYHYDROXYSTEARATE | 2.0 | — | 1.0 | 2.0 | — | — |
| BLUE 1 | — | — | — | — | 0.000060 | — |
| SILICA | — | — | — | 2.50 | — | — |
| POLYETHYLENE | — | — | — | 2.50 | — | — |

(% wt)* Overall weight percent of individual components present in the composition.

Evaluation of Inventive Compositions: Methods and Test Results

To determine which alcohol had the highest removing efficacy, small chain alcohols selected from ethanol, isopronol and butanol were tested. The removing efficacy was tested on artificial Deret Maybelline nail spoons which prior to the efficacy tests were treated with a water based nail enamel according to the procedure described below.
1. One coat of the water based nail enamel (described below) was applied on the nail spoons.
2. The nail spoons were left to air-dry for three minutes.
3. Second coat of the water based nail enamel was applied and left for 24 hours to air-dry.
4. The treated and dry nail spoons were subjected to the removal with selected alcohols.

Composition of water based nail polish used in the instant experiment contained: water, styrene/acrylates/ammonium methacrylate copolymers, glycol n-butyl ether, dipropylene glycol dibenzoate.

TABLE 2

Removal efficacy of ethanol, isopropanol and butanol

| Number of strokes/sample size* | Ethanol | Isopropanol | Butanol |
|---|---|---|---|
| Residue of nail polish after 5 strokes | XXXXX | XX | XXX |
| Number of strokes required to remove 2 coats of nail polish | 17 | 30 | 25 |

*Two (2) Maybelline nail spoons were used for each experiment

Cotton pads were treated with each of individually tested alcohols (ethanol, isopropanol, butanol) by flipping a bottle containing the alcohol and pouring some of it on the cotton pad. The alcohol treated pads were used to wipe off the water nail enamel by stroking the treated nail spoons. The first experiment involved using five strokes of the alcohol soaked cotton pads and the nail spoons were visually evaluated for the amount of the residue of the water based enamel. Further, during the second experiment, the alcohol treated cottons pads were used until the water nail enamel was completely removed from the nail spoons. The number of strokes required to remove the nail polish was recorded. The same procedure was repeated for each of the tested alcohols. The tests were conducted on the same day using the same procedures.

It was observed that the most effective tested monoalcohol was ethanol. Five strokes with the ethanol treated cotton pads removed the most of the water based nail polish composition. It was followed by butanol and isopropanol. Furthermore, in order to entirely remove two coats of the water based nail enamel with ethanol, the nail spoons had to be subjected to 17 strokes of ethanol treated cotton pads. It was followed by butanol which required 25 strokes and isopropanol with 30 strokes.

Based on the above described experiments it was concluded that from all three tested monoalcohols, ethanol was the most effective. Thus, it was used to be combined with the odorless base containing propylene glycol, propylene carbonate.

TABLE 3

Removal efficacy of nail remover compositions containing different ratios of ethanol and odorless base

| | sample size* | | | | | |
|---|---|---|---|---|---|---|
| Number of strokes | 100% ethanol/0% odorless base | 80% ethanol/20% odorless base | 60% ethanol/40% odorless base | 40% ethanol/60% odorless base | 20% ethanol/80% odorless base | 0% ethanol/100% odorless base |
| Residue of nail polish on nail | X | XXX | XXXXX | XX | X | 0 |

TABLE 3-continued

Removal efficacy of nail remover compositions
containing different ratios of ethanol and odorless base

| Number of strokes | sample size* | | | | | |
|---|---|---|---|---|---|---|
| | 100% ethanol/0% odorless base | 80% ethanol/20% odorless base | 60% ethanol/40% odorless base | 40% ethanol/60% odorless base | 20% ethanol/80% odorless base | 0% ethanol/ 100% odorless base |
| spoons after 5 strokes Number of strokes required to remove 2 coats of nail polish | 17 | 15 | 12 | 13 | 14 | 21 |

*Two (2) Maybelline nail spoons were used for each experiment

In order to determine composition of the most efficacious nail polish remover containing ethanol and the odorless base, different ratios (as previously disclosed) of ethanol and the odorless blend were tested. During the first part of the experiment, the nail spoons treated with the water based nail enamel were subjected to five strokes with cotton pads treated with a tested remover composition. Then, the nail spoons were visually evaluated for the presence of the residue of the water based enamel. Further, the second experiment involved the use of the tested remover blends until the water nail enamel was fully removed from the nail spoons. The same procedure was repeated for each of the tested mixtures. All experiments were conducted on the same day using the same procedure.

Based on the results provided in Table 3 it was observed that the least residue of the water based nail polish enamel after using five strokes was seen on the nail spoon samples after the use of 60% ethanol/400 odor free base gel. It was followed by the use of 80% ethanol/20% odor free base gel, 40% ethanol/60% odor free base gel and 100% of ethanol respectively. The use of 100% of odorless base did not show removal effect on the water based nail enamel.

The second part of the experiment indicated that the removal of the water based enamel with the remover containing 60% ethanol and 40% odorless base was the most effective and required 12 strokes to remove coating from the nail spoons. It was followed by the blend containing 40% ethanol/60% odorless base (13 strokes), 20% ethanol/80% odorless base (14 strokes) and 80% ethanol/20% odorless base (14 strokes). The use of 100% ethanol required 14 strokes and 100% of odorless base needed 21 strokes to entirely remove the water based nail enamel from the nail spoons.

TABLE 4

Removal effect of commercially available odorless and acetone deficient nail polish removers vs. inventive 60% ethanol/40% odorless base composition (acetone deficient)

| Number of stroke/sample size[1] | Scotch naturals oily remover | Karma naturals oily remover | Comparator 1 | 60% ethanol/ 40% odorless base* | 60% ethanol/ 40% odorless base in gel form*♦ |
|---|---|---|---|---|---|
| Removal of 2 coats of nail polish with 5 strokes | 0 | 0 | 0 | XXXX | XXXXX |
| Number of strokes required to remove 2 coats of nail polish | 25+ | 25+ | 25+ | 12 | 14 |

Tested comparative products:
Scotch Naturals oily remover: methyl soyate, dimethyl adipate, dimethyl glutarate
Karma Naturals oily remover: propylene carbonate, soybean oil methyl ester, tocopheryl acetate
[1]Two Maybelline nail spoons were used for each experiment
*compositions disclosed as above
♦ gel product was left on the treated nail spoon for 2 minutes before it was removed with the cotton pad.

Further, the removal efficacy of the inventive composition (60% ethanol/400 odorless base) versus above listed commercially available acetone deficient nail polish removers was tested. The cotton pads were treated with each of the remover compositions as per previous disclosure. The first experiment the nail spoons were stoked five times with the cotton pads treated with the tested remover. The artificial nail spoons were visually evaluated for the presence of the residue of the water based enamel. Then, in the second part of the experiment, the cotton pads treated with tested removers were used until the water nail enamel was wholly removed from the nail spoons. The same procedure was repeated for each of the tested compositions. All experiments were conducted on the same day using the same procedure.

Concerning the efficacy of different acetone deficient nail polish removers it appeared that 60% ethanol/40% odorless base gel was the most effective. 60% ethanol/40% odorless base gel left the least of the water based enamel residue on the nail spoons after being subjected to five strokes with the cotton pad. It was followed by 60% ethanol/40% odorless base liquid. The Comparator 1, Scotch Naturals oily remover and Karma Naturals oily remover appeared to be not effective in removal the water based nail enamel.

The results provided in Table 4 show that it required 12 strokes to remove the water based nail polish with the liquid form of 60% ethanol/40% odorless base. It was followed by the gel of 60% ethanol/400 odorless base with required 14 strokes. In contrast, comparator 1, Scotch Naturals oily remover and Karma naturals oily remover needed more than twenty five strokes to entirely remove the coating from the nail spoons. Table 4 shows the increased removal efficacy of the inventive compositions in comparison to other acetone deficient nail removal compositions.

What is claimed is:

1. An acetone deficient composition, comprising:
   (a) at least one odorless base comprising: from about 5% to 9% by weight, relative to the total weight of the composition, of at least one polyol selected from the group consisting of glycol, glycol ether and a mixture thereof;
   from about 30% to about 65% by weight, relative to the total weight of the composition of at least one $C_4$-$C_6$ cyclic carbonate; and
   from about 6% to about 9% by weight, relative to the total weight of the composition of at least one hydrocarbon based non-volatile oil;
   (b) from about 30% to about 65% by weight, relative to the total weight of the composition, of ethanol;
   (c) from about 0.5% to about 5% by weight, relative to the total weight of the composition, of at least one thickening polymer;
   (d) from about 0.5% to about 5% by weight, relative to the total weight of the composition, of at least one abrasive agent;
   (e) from about 0.1% to about 2% by weight, relative to the total weight of the composition, of at least one surfactant;
   (f) from about 0.1% to about 5% by weight, relative to the total weight of the composition, of at least one pigment; and
   (g) from about 0.5% to about 20% by weight, relative to the total weight of the composition, of water, wherein the weight ratio of at least one odorless base (a) to ethanol (b) is from about 60:40 to about 40:60.

2. The acetone deficient composition of claim 1, wherein the at least one hydrocarbon based non-volatile oil is selected from: $C_{10}$-$C_{26}$ monoalcohols, hydroxylated monoesters of a $C_2$-$C_8$ carboxylic acid and of a $C_2$-$C_8$ alcohol, hydroxylated diesters of a $C_2$-$C_8$ dicarboxylic acid and of a $C_2$-$C_8$ alcohol, hydroxylated triesters of a $C_2$-$C_8$ tricarboxylic acid and of a $C_2$-$C_8$ alcohol, esters of a $C_2$-$C_8$ polyol and of one or more $C_2$-$C_8$ carboxylic acids, and mixtures thereof.

3. A method of removing a water based nail polish enamel comprising applying the composition of claim 1 to a water based nail polish on a nail in an amount sufficient to remove polish from the nail.

4. A method of making an acetone deficient nail polish remover comprising combining:
   (a) at least one odorless base comprising: from about 5% to 9% by weight, relative to the total weight of the composition, of at least one polyol selected from the group consisting of glycol, glycol ether and a mixture thereof;
   from about 30% to about 65% by weight, relative to the total weight of the composition, of at least one $C_4$-$C_6$ cyclic carbonate; and
   from about 6% to about 9% by weight, relative to the total weight of the composition, of at least one hydrocarbon based non-volatile oil;
   (b) from about 30% to about 65% by weight, relative to the total weight of the composition, of ethanol;
   (c) from about 0.5% to about 5% by weight, relative to the total weight of the composition, of at least one thickening polymer
   (d) from about 0.5% to about 5% by weight, relative to the total weight of the composition, of at least one abrasive agent
   (e) from about 0.1% to about 2% by weight, relative to the total weight of the composition, of at least one surfactant
   (f) from about 0.1% to about 5% by weight, relative to the total weight of the composition, of at least one pigment; and
   (g) from about 0.5% to about 20% by weight, relative to the total weight of the composition, of water,
   wherein the weight ratio of at least one odorless base (a) to ethanol (b) is from about 60:40 to about 40:60.

* * * * *